United States Patent
Nehls et al.

(10) Patent No.: US 6,372,472 B1
(45) Date of Patent: Apr. 16, 2002

(54) FILTER MEDIA CONTAINING POWERED CELLULOSE AND IMMOBILIZED LIPASE FOR SWIMMING POOL AND SPA WATER FILTERATION

(75) Inventors: Barry L. Nehls; Karen A. Nehls, both of Toledo, OH (US)

(73) Assignee: Swim Pure Corporation, Toledo, OH (US)

( * ) Notice: Subject to any disclaimer, the term of this patent is extended or adjusted under 35 U.S.C. 154(b) by 0 days.

(21) Appl. No.: 09/406,018

(22) Filed: Sep. 24, 1999

(51) Int. Cl.[7] .......................... C12N 9/20; C12N 11/02; C12N 11/08; C12P 7/64; C02F 3/00
(52) U.S. Cl. .................. 435/198; 210/606; 435/134; 435/177; 435/180
(58) Field of Search .................. 435/174, 177, 435/179, 180, 198, 134; 210/606

(56) References Cited

U.S. PATENT DOCUMENTS

| | | | |
|---|---|---|---|
| 4,100,094 A | * 7/1978 | Burns et al. | 252/89 R |
| 5,221,469 A | 6/1993 | Nehls | 210/232 |
| 5,279,734 A | 1/1994 | Nehls | 210/295 |
| 5,399,265 A | 3/1995 | Nehls | 210/490 |
| 5,702,737 A | 12/1997 | Guzinski et al. | 426/32 |
| 5,773,256 A | 6/1998 | Pelenc et al. | 435/74 |
| 5,851,973 A | 12/1998 | Foley | 510/235 |

OTHER PUBLICATIONS

Novozym 435, Product Specification, Enzyme Business (8 pages).

* cited by examiner

Primary Examiner—David M. Naff
(74) Attorney, Agent, or Firm—Emch, Schaffer, Schaub & Porcello Co., L.P.A.

(57) ABSTRACT

A composition is provided containing powdered cellulose and at least one water insoluble, immobilized water treatment additive. Preferably, a filter media composition is provided containing powdered cellulose and at least one water insoluble, immobilized enzyme such as lipase for filtration of swimming pool and spa water. The lipase may be recombinantly produced, and lipases having 1,3 positional or non-positional specificity are used. The immobilized lipase may be in the form of bead-shaped particles, and immobilization can be on a macroporous acrylic resin. Moisture may be added to the composition to provide a pre-moistened composition that is dustless and provides for improved dispersement and even filter grid coating. In a filtering system, the filter media absorbs oils contained in pool or spa water, and the lipase hydrolyzes the oils.

18 Claims, No Drawings

FILTER MEDIA CONTAINING POWERED CELLULOSE AND IMMOBILIZED LIPASE FOR SWIMMING POOL AND SPA WATER FILTERATION

TECHNICAL FIELD

This invention relates to a cellulose filter media useful in normal swimming pool and spa filtration applications.

BACKGROUND ART

The motion picture industry helped pioneer the use of Diatomaceous Earth (D.E.) for filtering swimming pools. Filming underwater requires high water clarity for good visibility. Conventional flocculation and filtration through high rate sand units, available in the 1930's could not clarify the water sufficiently for quality filming. So, the industry experimented with D.E. media to improve the filtration process and achieve the desired underwater effects.

Many different types and styles of D.E. filters are available. Some are designed to be pressure backwashed. Saturated D.E. is flushed from the tank with water flow reversal, many utilizing an integral backwashing valve. Others feature easy internal access with quick opening band clamps and must be manually cleaned. Still other have filter bundles of square flat grids, curved filter grids, circular disks, or filter tubes. The health risk associated with the use of D.E., however, is free crystalline silica dust. Packages of D.E. now carry carcinogenic warning labels.

The oils (body oils, tanning oils, etc.) typically float on the surface of the water. In problematic pool and spa situations with high oil concentrations, significant quantities of oil simply flow through the filter and return to the vessel. This creates the illusion of lower long term operating pressures since so much of the light oils are not being trapped by the D.E. In fact, however, the oils that are trapped by the D.E. tend to bond the filter cake to the grids and eventually impregnate the grid material itself. The end result is large volumes of water needed to backwash (incompletely) the D.E. from the grids, fouled grids and increasing buildup of D.E. at the bottom of the filter. Unremoved oils will result in scum lines in the pool/spa and reduced water clarity. Continued operation with D.E. will require filter tear down, clean out and grid degreasing on a regular basis due to rising start-up pressure after each backwash. One solution to D.E.'s carcinogenic properties, problematic oil removal and filter caking tendencies has been the industry's use of cellulose filter media. Cellulose has a natural affinity for oils. Cellulose actually "wicks" the oils from the water, in lieu of merely trapping the oils as D.E. does. By absorbing the oils into the cellulose fiber cake, the oils are not permitted to reach the filter grid material, preventing filter fouling. Despite this improvement, heavy suntan oil usage and continuous backwashing of cellulose filter media continues to be a problem.

DISCLOSURE OF INVENTION

This composition is a combination of powdered cellulose and an effective amount of at least one water insoluble, immobilized water treatment additive. Preferably, it is a filter media comprising powdered cellulose and an effective amount of at least one water insoluble, immobilized enzyme. Generally, the powdered cellulose is pulverized alpha cellulose and the immobilized enzyme is from the lipase category of very large, complex protein molecules. Preferably, the lipase enzyme has been transferred from a strain of *Candida antarctica* to a host organism of *Aspergillus oryzae*. The lipase enzyme consists of bead-shaped particles with a diameter in the range of 0.3–0.9 mm and a bulk density ranging from 400 to 450 kg/m$^3$.

More preferably, the lipase enzyme shows 1,3 positional specificity or functions as a non-positional specific lipase. An acrylic resin immobilizes the enzyme. Preferably, a macroporous acrylic resin immobilizes the enzyme. Generally, the amount of immobilized enzyme ranges from 0.0001 to 0.10 weight percent. Preferably, the amount of immobilized enzyme ranges from 0.0001 to 0.01 weight percent. Specifically, the amount of immobilized enzyme is about 0.0225 weight percent.

The composition of this invention is a filter media composed of pulverized alpha cellulose (virgin) having an average (medium) fiber length of approximately to 60$\mu$ (microns). Typical degree of filtration is 2$\mu$–5$\mu$ in normal swimming pool and spa filtration applications. The appearance of the material is a white, fibrous flock, with little to no odor. Powdered cellulose, has the GRAS (generally recognized as safe) status of the U.S.F.D.A. for use as a food additive. In terms of disposal after use, it is biodegradable when it is backflushed from the filter.

Because the composition is composed of powdered cellulose as produced from virgin pulp stock, the filter media has a natural affinity for oils. To assist with the removal of body and tanning oils, lotions, etc. from typical pool water, it is enzyme enhanced. Blended into the product is an immobilized lipase (oil breaking) enzyme. This enzyme is water insoluble and remains in the filter media for continuous treatment of the pool water filtrate.

Enzymes are natural occurring protein molecules, active in such processes as composting, organic decomposition and food digestive processes. The enzyme blended into this composition is water insoluble, which means that the enzyme remains in the filter cake for continuous action and is not circulated into the pool. Typical enzyme "activity" for 6 months or more, resulting in a time released activity throughout the life of the filter media. Because the immobilized enzyme utilized is a food grade material and in a relatively low concentration, it remains a very safe, environmentally "friendly" product.

Other additives we can use alone or in combination with the enzymes include pH stabilizers, time release oxidizers, chemical stain removers, clarifiers, co-agulants, water conditioners and adsorptive materials.

BEST MODE OF CARRYING OUT INVENTION

The fibrous nature of the media ensures the complete cover of filter grids and septums resulting in 100% filtration and superior water quality. This natural coating ability also stops migration of filter powder back to the pool eliminating the usual "puff" upon filter start up. Its active "time release" enzyme action breaks up and removes body and tanning oils, gels and lotions. Floating oils are directed immediately to the filter system via the natural pool skimming action. The media absorbs the oils, "locking" them in the filter cake where treatment through enzymatic activity begins to work immediately.

The combined action of cellulose adsorption and enzyme treatment of oils results in significant reduction of oil scum lines and waterline rings in the pool or spa, continuous reduction of oils and other organic materials that clog the filter and reduces its efficiency and subsequent water clarity, water becomes crystal clear and odor free, and reduces chloramine build-up which causes red eye or skin irritations in chlorine treated pools.

Our composition is a dustless product, pre-moistened for superior wetting and dispersement. A dustless product eliminates housekeeping problems associated with the storage and use of other typical dry filter powders. The pre-moistened material prevents clumping and uneven filter grid coating. The non-abrasive filter media will not harm backwash valves, piping, heaters and pump seals. The filter is gentle on filter grids as well and will not lodge or plug filter fabric. The product saves water and pool chemicals through longer filter cycles and continuous, superior water clarity. With longer filter cycles, one will not be backwashing large volumes of chemically treated or heated water. When backwashing is required, the water volume is substantially reduced as the spent product is rapidly and easily washed from the filter. It is a lightweight product in pre-measured bags for proper dosage every time. As a lightweight product, it will not settle out in skimmer boxes, gutters and piping. As an additive for cartridge filters, the media provides the following continuous use benefits:

protects cartridge fabric from slimes and difficult to remove contaminates, enhances water clarity through depth filtration (versus barrier filtration of typical cartridge), increases dirty holding capacity of the cartridge(s), removes oils and other organic material through cellulose adsorption and enzymatic activity, and reduces cartridge cleaning time and labor.

As an additive for sand filters, it provides the following for occasional, periodic usage:

top coats the sand bed, improving filtration from average $30\mu$ to $5\mu$ clarity or better, removes oils and other organic material through cellulose adsorption and continuous enzymatic activity, removes finely suspended particulate in pool water that causes turbidity or cloudiness, especially after heavy bather load or unusually heavy pool use, and backwashes virtually 100% from the sand filter upon reversing flow.

The product saves time and labor in backwashing. As a low density product, it resists caking up in the filter, backwashes completely and easily from any D.E. style vacuum or pressure filter. Because it also releases completely from filter grids, typical tear downs are seldom required.

The enzyme (Novozym 435) is an immobilized preparation of a thermostable lipase. It is particularly useful in the synthesis of esters. It has a broad substrate specificity and promotes reaction between a wide range of primary and secondary alcohols and organic acids. The enzyme is a triacylglycerol hydrolase and at the same time acts as an effective carboxylesterase. The lipase is available with an activity of about 7000 propyl laureate units (PLU)/g. The product will be delivered with a water content of 1–2 weight percent.

The lipase is immobilized on a macroporous acrylic resin. Typically, acrylic resins are thermoplastic polymers or copolymers of acrylic acid, methacrylic acid, esters of these acids, acrylonitrile, or methyl methacrylate. The monomers are colorless liquids that polymerize readily in the presence of light, heat, or catalysts such as benzoyl peroxide.

As an organic catalyst, enzymes are not used up in the process and do not change the end point of the chemical reaction. During the operation, they attach to a given oil molecule, often called the substrate, and cause the chemical change that they are programmed to produce because of their molecular configuration. As soon as it is completed, the enzyme itself leaves this changed molecule and goes to the next substrate (oil) molecule. A proportion of about one enzyme molecule to a million substrate molecules appears to be sufficient to carry on normal enzymatic reaction.

The enzymes catalyze the hydrolysis of oils that are typically found contaminating pool and spa water, breaking them down (typically involves chemical breaking of number one and three carbon bonds), making the fragments water soluble. The typical tri-glyceride is broken into mono-glyceride and a pair of "free" fatty acids. The composition has a natural affinity for the oil through absorption, the enzymes break up the captured oil to keep the filter flowing free and the water sparkling clean.

In addition to the blending of the enzyme, a final product enhancement is the addition of an effective amount of moisture. Generally, the amount of moisture ranges up to 50 percent by weight.

Preferably, the addition is up to 25% by weight moisture. This addition renders the powered cellulose filter media a "dustless" product. The additional liquid content makes the product "pre-moistened", resulting in better and faster product dispersion into the pool or spa water and even coating of the filter grids and septums.

With these latest enhancements, the filter media now provides the following features and benefits as a direct substitute for D.E. or an additive to sand and cartridge filters: it is non-toxic, completely safe filter media for all D.E. style, cartridge and pool filters. No personal protection equipment or special storage/handling is required. Next to water, the product is the safest material for use in pools or spas. It is environmentally "friendly" and biodegradable when it leaves the pool filter. No separation tank is required. Several safe disposal options include direct sanitary discharge or discharge onto the lawn were the product will decompose after several weeks much like a grass clipping.

In addition to these embodiments, persons skilled in the art can see that numerous modifications and changes may be made to the above invention without departing from the intended spirit and scope thereof.

I claim:

1. A filter media composition for use in swimming pool water and spa water filtration consisting essentially of powdered cellulose and at least one water insoluble, immobilized lipase in an amount effective to catalyze hydrolysis of oil contaminating swimming pool water or spa water.

2. A composition according to claim 1 wherein the powdered cellulose is pulverized alpha cellulose.

3. A composition according to claim 1 wherein the lipase is recombinantly produced by transferring a gene encoding the lipase to *Aspergillus oryzae* as a host organism.

4. A composition according to claim 1 wherein the immobilized lipase consists of bead-shaped particles with a diameter in the range of 0.3–0.9 mm and a bulk density ranging from 400 to 450 kg m$^3$.

5. A composition according to claim 1 wherein the lipase shows 1,3 positional specificity.

6. A composition according to claim 1 wherein the lipase is a triacylglycerol hydrolase.

7. A composition according to claim 1 wherein the lipase has an activity of about 70000 PLU/g.

8. A composition according to claim 1 wherein the lipase is immobilized on an acrylic resin.

9. A composition according to claim 1 wherein the lipase is immobilized on a macroporous acrylic resin.

10. A composition according to claim 1 wherein the amount of immobilized lipase ranges from 0.0001 to 0.10 weight percent.

11. A composition according to claim 1 wherein the amount of immobilized lipase ranges from 0.0001 to 0.01 weight percent.

12. A composition according to claim 1 wherein the amount of immobilized lipase is about 0.0225 weight percent.

13. A composition according to claim 1 including an effective amount of moisture to provide a dustless composition.

14. A composition according to claim 1 including up to 50% by weight moisture.

15. A composition according to claim 1 including up to 25% by weight moisture.

16. A composition according to claim 1 further consisting essentially of at least one additive selected from the group consisting of pH stabilizers, time release oxidizers, chemical stain removers, clarifiers, co-agulants, water conditioners and adsorptive materials.

17. A composition according to claim 1 wherein the lipase is a non-positional specific lipase.

18. A composition according to claim 1 wherein the lipase is a carboxylesterase.

* * * * *